United States Patent
Kysilka et al.

(10) Patent No.: US 7,872,150 B2
(45) Date of Patent: Jan. 18, 2011

(54) PROCESS FOR THE PREPARATION OF AN OXALIPLATIN

(75) Inventors: Vladimir Kysilka, Brno (CZ); Jan Mengler, Praha (CZ); Petr Kacer, Praha (CZ); Libor Cerveny, Praha (CZ)

(73) Assignee: Vuab Pharma A.S. (CZ)

( * ) Notice: Subject to any disclaimer, the term of this patent is extended or adjusted under 35 U.S.C. 154(b) by 194 days.

(21) Appl. No.: 12/303,587

(22) PCT Filed: Jun. 8, 2006

(86) PCT No.: PCT/EP2006/005456

§ 371 (c)(1),
(2), (4) Date: Dec. 5, 2008

(87) PCT Pub. No.: WO2007/140804

PCT Pub. Date: Dec. 13, 2007

(65) Prior Publication Data

US 2010/0174102 A1     Jul. 8, 2010

(51) Int. Cl.
*C07F 15/00*     (2006.01)

(52) U.S. Cl. ..................... 556/137; 514/492

(58) Field of Classification Search ............... 556/137; 514/792
See application file for complete search history.

(56) References Cited

U.S. PATENT DOCUMENTS 4,169,846 A     10/1979   Kidani et al.
5,290,961 A *   3/1994    Okamoto et al. ............ 556/137

FOREIGN PATENT DOCUMENTS

| EP | 0 617 043 B1 | 9/1994 |
|----|--------------|--------|
| EP | 0 625 523 B1 | 11/1994 |
| EP | 0 801 070 A  | 10/1997 |
| EP | 1 308 454 A2 | 5/2003 |
| WO | WO 03/004505 A1 | 1/2003 |
| WO | WO 2005/035544 A1 | 4/2005 |

OTHER PUBLICATIONS

International Search Report dated Mar. 2, 2007, issued in international application No. PCT/EP2006/005456.

* cited by examiner

*Primary Examiner*—Porfirio Nazario Gonzalez
(74) *Attorney, Agent, or Firm*—Ostrolenk Faber LLP

(57) ABSTRACT

The present invention relates to an improved process for the preparation of oxaliplatin, the obtained oxaliplatin preparation and its use in cancer therapy.

14 Claims, No Drawings

PROCESS FOR THE PREPARATION OF AN OXALIPLATIN

CROSS REFERENCE TO RELATED APPLICATIONS

The present application is a 35 U.S.C. §371 National Phase conversion of PCT/EP2006/005456, filed Jun. 8, 2006. The PCT International Application was published in the English language.

TECHNICAL FIELD

The present invention relates to a process for preparing oxaliplatin, to an oxaliplatin preparation of high purity and its use in the treatment of cancer.

BACKGROUND OF THE INVENTION

Oxaliplatin, CAS Number [61825-94-3], is the generally used name for the (SP-4-2)-[(1R,2R)-1,2-cyclohexanediamine-kN,kN']-[ethanedioato(2-)-kO$^1$,kO$^2$]platinum(II) complex of the structural formula I:

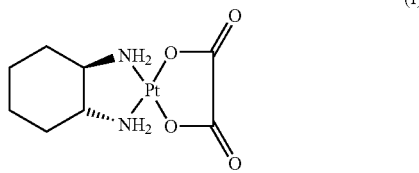

(I)

Oxaliplatin was first reported by the Nagoya City University, Japan, in Gann, 1976, 67(6), 921-2. Oxaliplatin is frequently used in cancer therapy. A general method for preparing oxaliplatin is described in prior art, e.g. in U.S. Pat. No. 4,169,846. The process described there is based on the reaction of a solid (SP-4-2)-dichloro-[(1R,2R)-1,2-cyclohexanediamine-kN,kN']platine(II) complex (in the following abbreviated as DACHPtCl$_2$) in water with two equivalents of silver nitrate, an elimination of the obtained solid phase and a subsequent reaction of the obtained [(1R,2R)-1,2-cyclohexanediamine-kN,kN']platinum(II) diaqua-complex dinitrate (in the following abbreviated as platinum(II) diaqua-complex dinitrate) with oxalic acid and/or its alkali metal salts. Analogous (SP-4-2)-diiodo- or dibromo-[(1R,2R)-1,2-cyclohexanediamine-kN,kN']platine(II) complex can be used instead of DACHPtCl$_2$ in this procedure but DACHPtCl$_2$ is the cheapest. The yield of the obtained oxaliplatin is usually between 60 to 70% and the final yield is usually between 40 to 50% after recrystallization. The platinum(II)diaqua-complex described above can thus be considered as a key synthetic intermediate for oxaliplatin preparation. It has the structural formula II and it is usually in the form of a dinitrate salt but another salts, e.g. sulphate salt, are possible:

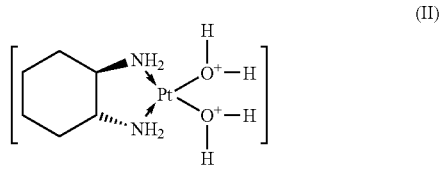

(II)

The above mentioned general procedure for preparing oxaliplatin has some serious drawbacks.

First drawback is a very long time procedure at room temperature. DACHPtCl$_2$ is a very low soluble in water. The dissolving of DACHPtCl$_2$ particles is very slow and the subsequent reaction with silver salt is very quick which leads to creating platinum(II) diaqua-complex dinitrate and the solid AgCl. Thus, the reaction is running in the thin liquid film on the surface of the particles of DACHPtCl$_2$ as a consequence of this fact and these particles are quickly covered by AgCl layer which blocks further reaction. That is why the reaction of DACHPtCl$_2$ with silver salt usually needs 1 to 3 days at room temperature to reach sufficient conversion according to prior art, e.g. WO 2005/035544 A1; WO 03/004505 A1; EP 1 308 454 A2. It is possible to partially reduce reaction time of DACHPtCl$_2$ with silver salts by increased amount of water and by increased reaction temperature but it is on account of lower yields and increased content of impurities.

Second drawback of the above mentioned general procedure is a high content of silver in prepared oxaliplatin which is usually greater than 100 p.p.m. Any of syntetic impurities, including silver ions, may cause severe adverse effects in the therapeutic use of oxaliplatin. Their presence is to be avoided and so, the prescripted limit for silver content in oxaliplatin is less than 5 p.p.m. Therefore, corresponding purification procedures are the subject of a great wealth of patents and patent applications. Among the most preferred purification processes are those, which use alkaline iodides for the elimination of silver ions and other impurities from the platinum (II) diaqua-complex dinitrate in combination with a large amount of water for the required re-crystallization and washing of the final product. Such a process is described for example in EP 0 617 043 61, WO 03/004505 and EP 0 625 523 B1. For the satisfactory elimination of the Ag$^+$ ions an about threefold excess of iodides is usually recommended. A serious drawback is, however, that iodides parallelly and predominantly react with a surplus of reactive platinum(II) diaqua-complex to the corresponding platinum(II)diiodo complex. These iodo species subsequently react with the spots of Ag$^+$ ions to form insoluble silver iodide precipitates. That is why this chemical purification method requires a considerable time, usually more than 15 hours, to reduce the content of Ag$^+$ ions in the final oxaliplatin below 5 p.p.m. This purification also leads to the contamination and coloration of the product by platinum (II)mono- and diiodo complexes. The crude oxaliplatin must therefore be re-crystallized from water. A further serious drawback results from the re-crystallization of oxaliplatin in water. A large amount of water and a temperature around the boiling point of water are necessary for the re-crystallization of the crude oxaliplatin. Finally, at the boiling point of water side products are easily formed from oxaliplatin even during the short time of the exposure, which represents another serious drawback. The yields of the re-crystallization of the product are less than 70%. If a repeated re-crystallization is necessary, a further loss of the product results. The purified re-crystallized oxaliplatin has still the content of silver ions above 1 p.p.m., usually from 2 to 5 p.p.m.

As follows from the above mentioned prior art, there is a great demand for a process to prepare oxaliplatin in a high purity by an effective method.

The technical problem underlying the present invention is therefore to provide a process for preparing oxaliplatin, which is simple and provides oxaliplatin with a high purity and simultaneously in a high yield.

SUMMARY OF THE INVENTION

The present invention solves the above-identified technical problem by providing a process for preparing oxaliplatin of the structural formula I

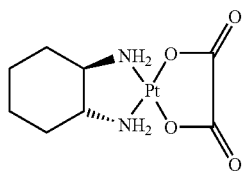

(I)

comprising the following steps:
a) reacting a (SP-4-2)dihalogen-[(1R,2R)-1,2-cyclohexanediamine-kN,kN']platinum(II) complex with a silver salt in an aqueous medium in the presence of a solid inert material to obtain an acidic aqueous solution containing [(1R,2R)-1,2-cyclohexanediamine-kN,kN']platinum(II) diaquacomplex and a solid phase,
b) removing the solid phase,
c) purifying the acidic aqueous solution containing [(1R,2R)-1,2-cyclohexanediamine-kN,kN']platinum(II) diaquacomplex obtained in step b) with a solid polymeric material containing cationic exchange groups to obtain a purified acidic aqueous solution and
d) adding oxalic acid and/or an oxalic salt to the purified acidic aqueous solution obtained in step c) to obtain purified oxaliplatin.

One first aspect of the invention is the use a solid inert material during the reaction step a). Thus, the invention foresees the use of a solid inert material in step a), which is able to be brought into contact with the reactants of step a), preferably by mixing, stirring and/or agitating the reaction mixture. In a particularly preferred embodiment, the inert material and the reaction solution of step a) form a suspension. The use of the inert solid material leads to a substantial reduction of reaction time, probably by an abrasion of the silver halogenid layer, e.g. AgCl layer, from the surface of $DACHPtCl_2$ particles. This reaction step takes preferably 0.5 to 5 hours at the preferred temperature range from 20 to 50° C. instead of 1 to 3 days at room temperature according to prior art. A particularly preferred temperature range is from 20 to 45° C. which leads to a complete conversion during 1 to 3 hours. In preferred embodiments various kinds of solid inert materials can be used, such as particulate materials, for instance powders, grain, balls, extrudates, granulates etc. These materials may for instance be materials conventionally used as inert catalyst carriers. In preferred embodiments, silicon dioxide and/or aluminium oxide, preferably Celite, can be used as a solid inert material. The solid inert material also improves removing of the solid AgCl after this reaction step. The solid inert material is preferably removed after step a) and before step c), preferably in step b), preferably by centrifugation or filtration.

A second aspect of the invention is the use of a solid polymeric material containing cationic exchange groups for purifying the acidic solution containing [(1R,2R)-1,2-cyclohexanediamine-kN,kN']platinum(II) diaqua-complex in step c). Solid polymeric material containing cationic exchange groups advantageously and surprisingly reduce the silver content in the purification step c) of the present process. We found in particular that the use of, in a particularly preferred embodiment, 5 mass. % of, in a further preferred embodiment, polyolefin microfibers containing styrene sulfonic acid groups, e.g. Smopex-101, with respect to the starting $DACHPtCl_2$ leads to one order decrease of silver content in platinum(II) diaqua-complex dinitrate during 1 hour at room temperature in step c).

DETAILED DESCRIPTION

In a preferred embodiment, the invention foresees that step c) of the present process is repeated at least once, in particular is carried out at least twice, three times or even more times. In a preferred embodiment, two purification cycles lead to the silver content in the purified acidic aqueous solution containing [(1R,2R)-1,2-cyclohexanediamine-kN,kN']platinum(II) diaquacomplex obtained in step c) below 0.1 p.p.m. and in the purified oxaliplatin obtained in step d) below 1 p.p.m. The similar purification effect has in a further preferred embodiment styrene-divinylbenzene co-polymers containing sulfonic acid groups, e.g. Dowex 50×8 but the amount of this ionex and the purification time should preferably be doubled in comparison with the use of polyolefin microfibers containing styrene sulfonic acid groups. The solid cationic polymeric material may preferably be used in particulate form, for instance used in form of a suspension. It may also be used in form of a cationic ion exchange chromatography, for instance as a resin in a column. The solid cationic polymeric material is preferably removed after step c) and before step d), for instance by centrifugation or filtration.

In a preferred embodiment of the present invention the amount of oxalic acid or oxalic salt is 0.9 to 1.1 equivalents with respect to the starting (SP-4-2)dihalogen-[(1R,2R)-1,2-cyclohexanediamine-kN,kN']platinum(II) complex in step d).

In a preferred embodiment of the present invention the reaction time is 2 to 6 hours at room temperature in step d).

In a preferred embodiment of the present invention the pH value in step d) is adjusted to 2.5-2.9, preferably 2.9, after adding of oxalic acid or oxalic salt. The pH value is decreased during the course of step d). In a preferred embodiment of the present invention oxaliplatin is washed with water to remove inorganic salts and subsequently with alifatic alcohol or aceton to remove organic impurities, in particular oxalic acid, and water to improve drying procedure. Oxaliplatin prepared according to the invention has prescripted pharmaceutical quality without need of re-crystallization which leads to a substantial loss of the expensive oxaliplatin.

In a preferred embodiment of the present invention (SP-4-2)dichloro-[(1R,2R)-1,2-cyclohexanediamine-kN,kN']platinum(II) complex is used as the starting (SP-4-2)dihalogen-[(1R,2R)-1,2-cyclohexanediamine-kN,kN']platinum(II) complex in step a). In a preferred embodiment the silver salt used in step a) is silver nitrate or silver sulphate.

In a further preferred embodiment of the present invention, the silver salt, in particular silver nitrate or silver sulphate, used in step a) is used in a stoichiometric amount in relation to the starting platinum(II) complex, e.g. per molar equivalent of the starting platinum(II) complex two molar equivalents of the silver nitrate or one molar equivalent of silver sulphate are used.

A third aspect of the invention is an oxaliplatin preparation with a specific impurity profile prepared according to the invention wherein the content of silver ions in oxaliplatin is less than 1 p.p.m. It is desirable to decrease impurities in oxaliplatin to the minimum level to decrease the possible adverse side effects during therapy with oxaliplatin to the minimum level. It is theoretically possible to decrease the content of silver ions in oxaliplatin below 1 p.p.m. according to prior art by purification process with iodides in the combination with repeated re-crystallization of the oxaliplatin but on account of a unacceptable loss of the very expensive oxaliplatin. Oxaliplatin prepared according to the invention has prescripted pharmaceutical quality without need of re-crystallization which leads to a substantial loss of the expensive oxaliplatin.

Thus, the present invention in particular provides in a preferred embodiment the advantage that the time for preparing oxaliplatin is decreased from days to hours. One further preferred embodiment of the present invention solves the above-identified problem with the above-identified process, wherein such a process provides a yield of oxaliplatin, which may be comparable in comparison to the prior art methods, but wherein the reaction time is substantially decreased and the purity is improved, i.e. higher than in the prior art. Compared to other prior art, the present invention solves the problem in another preferred embodiment, wherein the purity may be comparable in comparison to the prior art, but wherein the reaction time is substantially decreased and the yield is substantially better, i.e. higher than in the prior art.

The present invention in particular provides in a preferred embodiment the advantage that all of its process steps can be carried out using conventional water, or, in a particularly preferred embodiment, distilled water as an aqueous medium in step a) above. According to the present invention, it is not necessary to use deoxygenated water in any of its process steps. The present invention therefore provides a process for preparing oxaliplatin, according to which no deoxygenated water is used. In a particularly preferred embodiment, the process of the present invention is carried out under standard environmental conditions, in particular all and each process step of the present process is carried out in an environment, which is not using specific conditions, such as: a low oxygen atmosphere, or a vacuum, or an inert gas, or a nitrogen atmosphere, or a low oxygen atmosphere. The oxidizing power of spots of free oxygen present e.g. in water is negligible with respect to nitrates and/or nitric acid being present in stoichiometric amount during the preparation of the platinum(II) diaqua-complex dinitrate in step a) and/or oxaliplatin in step d).

Thus, the present invention provides in a quick and simple manner a preparation of oxaliplatin, which is highly pure, in particular, essentially pure. In the context of the present invention, "essentially pure" means that the oxaliplatin preparation obtained has a purity of at least 97.5%, preferably at least 98%, preferably at least 98.5%, even more preferably at least 99%, most preferably at least 99.5% (percentage values given according to the present teaching are mass %, i.e. mass/mass or weight/weight, i.e. w/w percentage determined by HPLC, if not otherwise indicated), that means other compounds except for the oxaliplatin are present only in the above identified specified minor amounts. In another preferred embodiment, the degree of impurity is in overall terms most preferably at maximum 2.5%, 2.0%, or 1.5%, more preferably at maximum 1.0%, in particular 0.5%.

In a preferred embodiment, the amount of oxalic acid (reaction component) in the oxaliplatin preparation is at maximum 0.2%, in particular at maximum 0.1%, more preferably at maximum 0.05%.

The amount of platinum(II) diaqua-complex (synthetic intermediate II) in the oxaliplatin preparation is in a preferred embodiment at maximum 0.10%.

The amount of dihydroxy platinum IV-complex (product of oxidation of oxaliplatin) in the oxaliplatin preparation is in a preferred embodiment at maximum 0.05%.

In a preferred embodiment of the present invention, the total amount of the above-identified mentioned three impurities, oxalic acid, platinum(II) diaqua complex and the dihydroxy platinum (IV) complex in the oxaliplatin preparation, is at maximum 0.30%.

Furthermore, the amount of the reverse S,S-enantiomer of oxaliplatin is in a preferred embodiment at maximum 0.10%.

The amount of hydroxo-bridge platinum-complex dimer and other detectable impurities in the oxaliplatin preparation is in a preferred embodiment at maximum 0.10%.

The amount of silver in the oxaliplatin preparation is in a preferred embodiment less than 1 p.p.m.

In a preferred embodiment, the total content of oxaliplatin-related impurities in the product according to the invention is less than 0.30%.

In a further preferred embodiment the total yield of the final product is at least 60%, preferably at least 65%, and most preferred at least 70% (w/w), based on the starting $DACHPtCl_2$.

Thus, in a preferred embodiment of the present invention, the subject-matter of this invention is a very quick, simple and effective method for the preparation of oxaliplatin of the structural formula I:

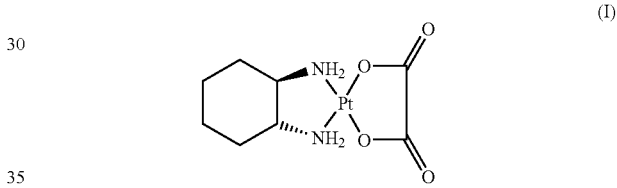

by the reaction of a (SP-4-2)dihalogen-[(1R,2R)-1,2-cyclohexanediamine-kN,kN']platinum(II) complex with a corresponding amount of a silver salt in the presence of a solid inert material, removal of the solid phase, i.e. in particular the precipitated silver compounds, purification of the acidic aqueous solution containing the corresponding platinum(II) diaqua-complex (structural formula II) with a solid polymeric material containing cationic exchange groups, adding oxalic acid or its salts to the purified acidic aqueous solution, wherein, in a preferred embodiment the pH-value is adjusted to 2.8 to 2.9, after adding oxalic acid or its salts and the resulting oxaliplatin is separated in a high purity and yield. Oxaliplatin prepared according to the invention has a high purity and needs no additional re-crystallization steps from water.

In a further preferred embodiment of the present invention the silver salt used in step a) is silver nitrate ($AgNO_3$) or silver sulphate ($Ag_2SO_4$).

In a preferred embodiment of the present invention, the content of $Ag^+$ in oxaliplatin is less than 1 p.p.m.

In a particularly preferred embodiment of the present invention, in step c), that means for the purification of the acidic aqueous solution to obtain a purified acidic aqueous solution 2 or 3 purification steps are conducted without substantial loss of the product.

The process of the present invention can, in a preferred embodiment of the present invention, be conducted in water in the absence of light, in particular visible light.

The present invention also foresees a pharmaceutical composition comprising an oxaliplatin preparation of the present invention together with at least one pharmaceutically acceptable carrier and optionally further additives.

Furthermore, the present invention provides the use of an oxaliplatin preparation according to the present invention for the preparation of a pharmaceutical composition for the treatment of cancer.

Further preferred embodiments are the subject-matter of the sub-claims.

The invention will be further explained in more detail by way of examples. These examples are illustrative only and do in no way limit the scope of the invention defined in the claims and the contents of the present description.

EXAMPLES

Example 1

All procedures were carried out in the absence of light.

A mixture of 3.88 g of fine powdered DACHPtCl$_2$ 98% (10 mmol), 1.55 g purified Celite, 3.41 g AgNO$_3$ 99.5% (20 mmol) and 27 ml purified water was intensively stirred 5 minutes at room temperature and then 2 hours at 45° C. The suspension was cooled to 3° C. and then filtered through the plate with active charcoal. The crude acidic filtrate had the content of silver ions 0.0018 mass. %, i.e. 18 p.p.m. 0.19 g of Smopex-101 was added to the crude filtrate and the suspension was stirred 1 hour at room temperature. The solid fraction was then removed by filtration. The purifying procedure with Smopex-101 was repeated once again and the purified solution was then filtered through an ultrafilter with the porosity 0.22 μm. 1.27 g oxalic acid dihydrate 99.5% (10 mmol) was added to the purified solution, pH value was adjusted to 2.9 by means of 40% solution of KOH, the mixture was stirred 4 hours at room temperature and the resulting suspension was cooled to 3° C. The final solid oxaliplatin was separated by filtration, washed four times with 5 ml ice water and four times with 5 ml ethanol. Oxaliplatin was dried under nitrogen flow at 40° C. to the constant weight.

The yield of oxaliplatin was 2.80 g (70.5% based on starting DACHPtCl$_2$). The appearance of the product was white. The content of silver was less than 0.00005 mass %, i.e. 0.5 p.p.m., the content of oxalic acid was 0.04%, the content of platinum(II) diaqua-complex was 0.08%, and the total content of related impurities was 0.22% (by HPLC method).

Example 2

The same procedure according to Example 1 with exception that 0.39 g Dowex 50×8 in H-cycle was used instead of 0.19 g Smopex-101 for purifying of the crude filtrate and that time of purification was 2 hours instead of 1 hour.

The yield of oxaliplatin was 2.50 g (62.9% based on starting DACHPtCl$_2$). The appearance of the product was white. The content of silver was 0.0001 mass %, i.e. 1 p.p.m., the content of oxalic acid was 0.04%, the content of platinum(II) diaqua-complex was 0.09%, and the total content of related impurities was 0.25% (by HPLC method).

Example 3

Comparative, without Celite

The same procedure according to Example 1 with exception that no Celite was used in the procedure. The crude acidic filtrate had the content of silver ions 0.2500 mass. %, i.e. 2500 p.p.m.

The yield of oxaliplatin was 2.60 g (65.5% based on starting DACHPtCl$_2$). The appearance of the product was white. The content of silver was 0.0220 mass %, i.e. 220 p.p.m.

Example 4

Comparative, According to Prior Art

All procedures were made at room temperature in the absence of light.

A mixture 3.88 g of fine powdered DACHPtCl$_2$ 98% (10 mmol), 3.41 g AgNO$_3$ 99.5% (20 mmol) and 27 ml purified water was intensively stirred 70 hours at room temperature. The suspension was cooled to 3° C. and then filtered through the plate with active charcoal. The crude acidic filtrate had the content of silver ions 0.0060 mass. %, i.e. 60 p.p.m. 0.17 g potassium iodide (1 mmol) was added to the filtrate and stirred for additional 15 hours. Active charcoal in an amount of 0.1 g was then added, the suspension was stirred for another 1 hour and then the solid fraction was removed by filtration. The purified solution was filtered through an ultrafilter with the porosity 0.22 μm. 1.27 g oxalic acid dihydrate 99.5% (10 mmol) was added to the purified solution, the mixture was stirred 4 hours at room temperature and the resulting suspension was cooled to 3° C. The final solid oxaliplatin was separated by filtration, washed four times with 5 ml ice water and four times with 5 ml ethanol. Oxaliplatin was dried under nitrogen flow at 40° C. to the constant weight.

The yield of oxaliplatin was 2.51 g (63.2% based on starting DACHPtCl$_2$). The content of silver was 0.0004 mass %, i.e. 4 p.p.m. but the appearance of the product was light yellow.

The light yellow oxaliplatin was re-crystallized from hot water (1 mass part of oxaliplatin and 42 mass part of water). The hot solution was ultrafiltered, cooled to 3° C., the solid product was separated by filtration and washed three times with 5 ml of ice water. The oxaliplatin was dried under nitrogen flow at 40° C. to the constant weight. The yield was 1.60 g (40.3% based on the starting DACHPtCl$_2$). The appearance of the product was white. The content of silver was 0.0002 mass %, i.e. 2 p.p.m., the content of oxalic acid was 0.03%, the content of platinum(II) diaqua-complex was 0.10%, and the total content of related impurities was 0.21% (by HPLC method).

What is claimed is:

1. A process for preparing oxaliplatin of the structural formula I:

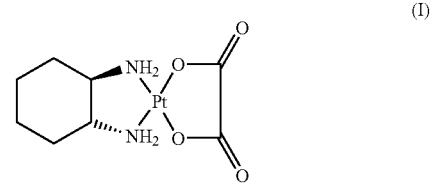

comprising the following steps:
 a) reacting a (SP-4-2)dihalogen-[(1R,2R)-1,2-cyclohexanediamine-kN,kN']platinum(II) complex with a silver salt in an aqueous medium in the presence of a solid inert material to obtain an acidic aqueous solution containing [(1R,2R)-1,2-cyclohexanediamine-kN,kN']platinum (II) diaquacomplex and a solid phase,
 b) removing the solid phase, c) purifying the acidic aqueous solution containing [(1R,2R)-1,2-cyclohexanediamine-kN,kN']platinum(II) diaquacomplex obtained in step b) with a solid polymeric material containing cationic exchange groups to obtain a purified acidic aqueous solution and d) adding at least one of an oxalic acid and an oxalic salt to the purified acidic aqueous solution obtained in step c) to obtain purified oxaliplatin.

2. The process according to claim 1, wherein the solid inert material in step a) is at least one of silicon dioxide and aluminium oxide.

3. The process according to claim 1, wherein step a) is carried out for 0.5 to 5 hours at temperature range of 0 to 50° C.

4. The process according to claim 1, wherein the solid polymeric material containing cationic exchange groups in step c) is polyolefin microfibers containing styrene sulfonic acid groups or styrene-divinylbenzene co-polymers containing sulfonic acid groups.

5. The process according to claim 1, wherein the purification step c) is repeated at least once.

6. The process according to claim 1, wherein 0.9 to 1.1 equivalents of oxalic acid or oxalic salt are used with respect to the starting (SP-4-2)dihalogen-[(1R,2R)-1,2-cyclohexanediamine-kN,kN']platinum(II) complex in step d).

7. The process according to claim 1, wherein the pH value in step
  d) is adjusted to 2.5-2.9 following addition of oxalic acid or oxalic salt.

8. The process according to claim 1, wherein step d) is carried out for 2 to 6 hours at room temperature.

9. The process according to claim 1, wherein the purified oxaliplatin in step d) is isolated from the purified acidic aqueous solution.

10. The process according to claim 1, wherein the oxaliplatin obtained in step d) is subsequently washed at least once.

11. The process according to claim 1, wherein the oxaliplatin obtained in step d) is washed at least once with water, and then subsequently washed with aliphatic alcohol or acetone.

12. The process according to claim 1, wherein (SP-4-2) dichloro-[(1R,2R)-1,2-cyclohexanediamine-kN,kN']platinum(II) complex is used as the starting (SP-4-2)dihalogen-[(1R,2R)-1,2-cyclohexanediamine-kN,kN']platinum(II) complex in step a).

13. The process according to claim 1, wherein a stoichiometric amount of the silver salt in respect to the amount of the starting (SP-4-2)dihalogen-[(1R,2R)-1,2-cyclohexanediamine-kN,kN']platinum(II) complex is used in step a).

14. The process according to claim 3 wherein step a) is carried out at a temperature range of 20° C. to 45° C.

* * * * *